United States Patent
Khoo et al.

(10) Patent No.: US 11,844,768 B2
(45) Date of Patent: Dec. 19, 2023

(54) TERAMEPROCOL AND NORDIHYDROGUAIARETIC ACID (NDGA) DERIVATIVES AS CORONAVIRUS ANTI-VIRAL AGENTS

(71) Applicant: Erimos Pharmaceuticals, LLC, Houston, TX (US)

(72) Inventors: Jeffrey Khoo, Singapore (SG); Stephan D. Glenn, Weston, FL (US)

(73) Assignee: Erimos Pharmaceuticals, LLC, Houston, TX (US)

( * ) Notice: Subject to any disclaimer, the term of this patent is extended or adjusted under 35 U.S.C. 154(b) by 0 days.

(21) Appl. No.: 17/576,075

(22) Filed: Jan. 14, 2022

(65) Prior Publication Data

US 2022/0233466 A1 Jul. 28, 2022

Related U.S. Application Data

(60) Provisional application No. 63/139,296, filed on Jan. 19, 2021.

(51) Int. Cl.
*A61K 31/09* (2006.01)
*A61P 31/14* (2006.01)
*A61K 31/05* (2006.01)

(52) U.S. Cl.
CPC .............. *A61K 31/09* (2013.01); *A61K 31/05* (2013.01); *A61P 31/14* (2018.01)

(58) Field of Classification Search
CPC .............. A61K 31/407; A61K 31/4709; A61K 9/0014; A61K 9/0019; A61K 9/0078; A61K 9/19

See application file for complete search history.

(56) References Cited

U.S. PATENT DOCUMENTS

| | | | |
|---|---|---|---|
| 8,178,527 B2 | 5/2012 | Chen et al. |
| 8,232,277 B2 | 7/2012 | Chen et al. |
| 8,568,728 B2 | 10/2013 | Jeffrey |
| 8,877,060 B2 | 11/2014 | Sehgal |
| 9,067,875 B2 | 6/2015 | Chen et al. |
| 9,481,660 B2 | 11/2016 | Heller et al. |
| 9,790,269 B2 | 10/2017 | Jiang et al. |
| 2005/0049194 A1 | 3/2005 | Frisen et al. |
| 2006/0040879 A1 | 2/2006 | Kosak |
| 2007/0060499 A1 | 3/2007 | Kosak |

(Continued)

OTHER PUBLICATIONS

International Search Report and Written Opinion for the counterpart PCT Application No. PCT/US2022/012297 dated Mar. 30, 2022 (11 pages).

(Continued)

*Primary Examiner* — Savitha M Rao
(74) *Attorney, Agent, or Firm* — Karen Canaan; CanaanLaw, P.C.

(57) ABSTRACT

Nordihydroguaiaretic acid (NDGA) derivatives, including terameprocol (TMP) have utility as anti-viral agents for use on patients infected with or at risk of infection with a coronavirus, including SARS-CoV-2. In vitro studies show coronavirus-infected cells treated with 0.2 µM-20 µM TMP show reduced viral RNA activity in vitro. Treatment-related cytotoxicity is not shown at 0.2 µM TMP with a low percentage of cytotoxicity shown at 5 µM TMP. In application, the NDGA derivatives may be administered to a patient intravenously at a molar concentration of 0.1-50 µM or orally at a molar concentration of 0.1-100 µM.

22 Claims, 8 Drawing Sheets

(56) References Cited

U.S. PATENT DOCUMENTS

2009/0155349 A1    6/2009   Heller et al.
2020/0276140 A1    9/2020   Glick et al.

OTHER PUBLICATIONS

Panit et al., In Silico studies reveal potential antiviral activity of phytochemicals from medicinal plants for the treatment of COVID-19 infection, Research Square, pp. 1-31 (2020).

Wankar et al., Role of Nanomedicine in Management and Prevention of COVID-19, Frontiers in Nanotechnology 2 (589541):1-6 (2020).

Rani et al., Self-Emulsifying Oral Lipid Drug Delivery Systems: Advances and Challenges, AAPA PharmSciTech 20 (129):1-12 (2019).

Dey et al., Multiparticulate Drug Delivery Systems for Controlled Release, Tropical Journal of Pharmaceutical Research 7(3):1067-1075 (2008).

Accelerated Emergency Use Authorization (EUA) Summary ORIG3N Novel Coronavirus (COVID-19) Test, ORIG3N, Inc., 2020.

Blecha et al., Inhibition of IGF-1R and lipoxygenase by nordihydroguaiaretic acid (NDGA) analogs, Bioorganic & Medicinal Chemistry Letters 17(4):4026-4029 (2017) (Abstract).

Cannalire et al., SARS-CoV-2 Entry Inhibitors: Small Molecules and Peptides Targeting Virus or Host Cells, International Journal of Molecular Sciences 21:5707 (pp. 1-27) (2020).

Carrossino et al., Spatiotemporal analysis of SARS-CoV-2 in K18-hACE2, pp. 1-75 (Preprint Sep. 23, 2021), available at https://doi.org/10.1101/2021.01.13.425144.

Chang et al., Reversal of multidrug resistance by two nordihydroguaiaretic acid derivatives, M4N and maltose-M3N, and their use in combination with doxorubicin or paclitaxel, Cancer Chemother Pharmacol, pp. 1-14 (2006). DOI 10.1007/s00280-006-0214-9.

Chen et al., Antiviral Activities of Methylated Nordihydroguaiaretic Acids. 2. Targeting Herpes Simplex Virus Replication by the Mutation Insensitive Transcription Inhibitor Tetra-O-methyl-NDGA, J. Med. Chem. 41(16):3001-3007 (1998).

Eads et al., Terameprocol, a methylated derivative of nordihydroguaiaretic acid, inhibits production of prostaglandins and several key inflammatory cytokines and chemokines, Journal of Inflammation 6:2 (pp. 1-18) (2009).

Grossman et al., Phase I study of terameprocol in patients with recurrent high-grade glioma, Neuro-Oncology 14(4):511-517 (2012).

John et al., Facile synthesis and nanoscale features of a nanostructured nordihydroguaiaretic acid analog for therapeutic applications, J Nanobiotechnol 18:74 (pp. 1-16) (2020).

Kalepu et al., Insoluble drug delivery strategies: review of recent advances and business prospects, Acta Pharmaceutica Sinica B 5;5(5):442-453 (2015).

Lu et al., Molecular mechanisms and clinical applications of nordihydroguaiaretic acid (NDGA) and its derivatives: An update, Med Sci Monit. 16(5):RA93-R100 (2010).

Merino-Ramos et al., Antiviral Activity of Nordihydroguaiaretic Acid and Its Derivative Tetra-O-Methyl Nordihydroguaiaretic Acid against West Nile Virus and Zika Virus, Antimicrobial Agents and Chemotherapy 61(8):1-10 (2017).

Meyers et al., Synthesis, Characterization and Anti-Melanoma Activity of Tetra-O-substituted Analogs of Nordihydroguaiaretic Acid, Bioorg Med Chem Lett. 19(16):4752-4755 (2009).

Ogando et al., SARS-coronavirus-2 replication in Vero E6 cells: replication kinetics, rapid adaptation and cytopathology (Preprint Apr. 20, 2020), available at https://doi.org/10.1101/2020.04.20.049924.

Oyegunwa et al., Tetra-O-methyl nordihydroguaiaretic acid (Terameprocol) inhibits the NF-kB-dependent transcription of TNF-a and MCP-1/CCL2 genes by preventing RelA from binding its cognate sites on DNA, Journal of Inflammation 7:59 (2010).

Park et al., Inhibition of HSV-1 replication and reactivation by the mutation-insensitive transcription inhibitor tetra-O-glycyl-nordihydroguaiaretic acid, Antiviral Research 58:35-45 (2003).

Pollara et al., Inhibition of poxvirus growth by Terameprocol, a methylated derivative of nordihydroguaiaretic acid, Antiviral Research 88:287-295 (2010).

Pruijssers et al., Remdesivir Inhibits SARS-CoV-2 in Human Lung Cells and Chimeric SARS-CoV Expressing the SARSCoV-2 RNA Polymerase in Mice, Cell Reports 32:107940 (pp. 1-6) (2020).

Rathnayake et al., 3C-like protease inhibitors block coronavirus replication in vitro and improve survival in MERS-CoV-infected mice, Sci. Transl. Med. 12:eabc5332 (pp. 1-12) (2020).

Soto-Acosta et al., Nordihydroguaiaretic acid (NDGA) inhibits replication and viral morphogenesis of dengue virus, Antiviral Research 109:132-140 (2014) (Abstract).

Stone et al., Stenoparib, an Inhibitor of Cellular Poly(ADP-Ribose) Polymerase, Blocks Replication of the SARS-CoV-2 and HCoVNL63 Human Coronaviruses In Vitro, Therapeutics and Prevention 12(1):e03495-20 (pp. 1-12) (2021).

Van Dyke et al., The Effect of Minnelide against SARS-CoV-2 in a Murine Model (Preprint May 6, 2021), available at https://doi.org/10.1101/2021.05.05.442875.

White et al., Plitidepsin has potent preclinical efficacy against SARS-CoV-2 by targeting the host protein eEF1A, Science 371:926-931 (2021).

Whitman et al., Structure-Activity Relationship Studies of Nordihydroguaiaretic Acid Inhibitors toward Soybean, 12-Human, and 15-Human Lipoxygenase, J. Med. Chem. 45:2659-2661 (2002).

TERAMEPROCOL AND NORDIHYDROGUAIARETIC ACID (NDGA) DERIVATIVES AS CORONAVIRUS ANTI-VIRAL AGENTS

CROSS-REFERENCE TO RELATED APPLICATIONS

This application claims priority under 35 U.S.C. § 119(e) to U.S. Provisional Patent Application No. 63/139,296, filed on Jan. 19, 2021, which is incorporated herein in its entirety.

TECHNICAL FIELD

The present invention relates generally to coronavirus anti-viral agents and more specifically, to the ability of nordihydroguaiaretic acid (NDGA) derivatives, such as terameprocol (TMP), to inhibit in vitro replication of coronavirus RNA.

BACKGROUND OF THE INVENTION

Coronavirus disease 2019 (COVID-19) is a contagious disease that is caused by infection with the severe acute respiratory syndrome coronavirus 2 (SARS-CoV-2). COVID-19 spreads from person to person through the respiratory route and affects both the upper respiratory tract (sinuses, nose, throat) and the lower respiratory track (windpipe and lungs). Initially, the lungs are the organs most affected by COVID-19 because the virus accesses host cells via the enzyme angiotensin-converting enzyme 2 (ACE2), which is most abundant in type II alveolar cells of the lungs. In some patients the virus infection spreads to other organs and tissues. The virus uses a special surface glycoprotein called a "spike" (peplomer) to connect to ACE2 and enter the host cell. The density of ACE2 in each tissue correlates with the severity of the disease in that tissue. As the alveolar disease progresses, respiratory failure might develop and death may follow. Although SARS-CoV-2 has a tropism for ACE2-expressing epithelial cells of the respiratory tract, patients with severe COVID-19 have symptoms of systemic hyperinflammation. Clinical laboratory findings of elevated IL-2, IL-7, IL-6, granulocyte-macrophage colony-stimulating factor (GM-CSF), interferon-γ inducible protein 10 (IP-10), monocyte chemoattractant protein 1 (MCP-1), Macrophage inflammatory protein 1-α (MIP-1α), and tumor necrosis factor-α (TNF-α) indicative of cytokine release syndrome (CRS) suggest an underlying immunopathology. HCoV-NL63 (NL63) is another species of coronavirus that was discovered in 2004 in a seven-month-old child with bronchiolitis. Similar to SARS-CoV-2, NL63 is an enveloped, positive-sense, single-stranded RNA virus that enters its host cell by binding to ACE2.

While several vaccines have been produced for immunization to SARS-CoV-2, the period of protection of these vaccines is unknown and will likely vary within the general population; thus, patients contracting COVID-19 are in need of treatments. Presently, remdesivir (trade name VEKLURY®, Gilead Sciences, County Cork, Ireland) is the only drug that has been approved by the United States Food and Drug Administration (FDA) for treatment of COVID-19. Remdesivir was approved for medical use in the United States in October 2020. In November 2020, the FDA granted emergency use authorization for the drug (tradename BARICITINIB®, Eli Lily and Company, Indianapolis, IN, USA) to be given to certain patients hospitalized with suspected or confirmed COVID-19, but only in combination with remdesivir. There remains a need for other drugs that can be used to treat COVID-19 and illnesses caused by NL-63 and other coronaviruses.

SUMMARY OF THE INVENTION

In one aspect, the present invention overcomes the need in the art by providing a method comprising administering a nordihydroguaiaretic acid (NDGA) derivative to a patient infected with or at risk of infection with a coronavirus.

In another aspect, the present invention overcomes the need in the art by providing a method comprising administering terameprocol (TMP) to a patient infected with or at risk of infection with a coronavirus.

In a further aspect, administration of the NDGA derivative inhibits viral RNA replication.

In another aspect, administration of the TMP inhibits viral RNA replication.

In one embodiment, the coronavirus is selected from the group consisting of human coronavirus NL63 (HCoV-NL63), human coronavirus 229E (HCoV-229E), human coronavirus OC43 (HCoV-OC43), human coronavirus HKU1 (HCoV-HKU1), Middle East respiratory syndrome-related coronavirus (MERS-CoV), severe acute respiratory syndrome coronavirus (SARS-CoV-1), and severe acute respiratory syndrome coronavirus 2 (SARS-CoV-2).

In another embodiment, the NDGA derivative is selected from the group consisting of terameprocol, 3'-O-methyl NDGA, tetra acetyl NDGA, maltose-tri-O-methyl NDGA, tetra-O-glycyl NDGA, bis-cyclic sulfate NDGA; bis-cyclic carbonate NDGA; methylenedioxyphenyl NDGA; tetra acetate NDGA.

In a further embodiment, the NDGA derivative is prepared by adding a constituent group (Z) to one or more of positions 2, 3, 4, 5, 6, 2', 3', 4', 5', and 6' in the NDGA structure of Formula (1):

wherein Z is: independently selected from the group consisting of methyl, ethyl, acetyl, butyryl, isobutyryl, valeryl, hexanoyl, propionyl, piperidin-1-yl, acetonide, fluoro, morpholino, hydroxyl, methoxyl, hydroxy-methoxyl, dimethyl, dihydroxyl, dimethoxyl, dimethylamino, diethylamino, trimethoxyl, groups, chlorine, bromine, nitrite, amino, and acetamido; $(CH_2)_x$Hal, wherein x is an integer of 1-10 and Hal is a halogen atom; $(CH_2CH_2O)_y$, wherein y is an integer of 1-10; or a carbamate-group.

In another embodiment, the NDGA derivative is formed into solid colloidal nanoparticles with a size in the range of 1-100 nanometers.

In a further embodiment, the TMP is formed into solid colloidal nanoparticles with a size in the range of 1-100 nanometers.

In another embodiment, the NDGA derivative is solubilized in a solution or suspension comprising a compound selected from the group consisting, (2-hydroxypropyl)-β- cyclodextrin, medium chain triglycerides, glyceryl monooleate, D-α-tocopheryl polyethylene glycol succinate, dimethylacetamide, dimethylsulfoxide, polypropylene glycol, polyethylene glycol 400, polysorbate 20, naringin, macrogol-15-hydroxystearate, and combinations thereof.

In a further embodiment, the TMP is solubilized in a solution or suspension comprising a compound selected from the group consisting (2-hydroxypropyl)-β-cyclodextrin, medium chain triglycerides, glyceryl monooleate, D-α-tocopheryl polyethylene glycol succinate, dimethylacetamide, dimethylsulfoxide, polypropylene glycol, polyethylene glycol 400, polysorbate 20, naringin, macrogol-15-hydroxystearate, and combinations thereof.

In another embodiment, the NDGA derivative is in a formulation for intravenous or oral administration.

In a further embodiment, the formulation for intravenous administration comprises 0.1-50 µM of the NDGA derivative.

In another embodiment, the formulation for the oral administration comprises 0.1-100 µM of the NDGA derivative.

In a further embodiment, the TMP is formulated as a solution for intravenous administration.

In another embodiment, the solution for intravenous administration comprises 0.1-50 µM of the TMP.

In a further embodiment, the solution for intravenous administration comprises the TMP solubilized in an aqueous solution comprising (2-hydroxypropyl)-β-cyclodextrin.

In another embodiment, the solution for intravenous administration has 1-10 mg/mL of TMP solubilized in an aqueous solution comprising 20-50% (2-hydroxypropyl)-β-cyclodextrin.

In a further embodiment, the solution for intravenous administration has 6 mg/mL of the TMP solubilized in an aqueous solution comprising 30% (2-hydroxypropyl)-β-cyclodextrin.

In another embodiment, the TMP is formulated for oral administration.

In a further embodiment, the formulation for oral administration comprises 0.1-100 µM of the TMP.

In another embodiment, the solution for oral administration comprises the TMP solubilized in a suspension comprising a medium chain triglyceride and D-α-tocopheryl polyethylene glycol succinate.

In a further embodiment, the solution for oral administration comprises 100-500 mg/mL of TMP solubilized in a suspension comprising a medium chain triglyceride and 50-100 mg/mL of D-α-tocopheryl polyethylene glycol succinate.

In another embodiment, the solution for oral administration comprises 300 mg/mL of TMP solubilized in a suspension comprising a medium chain triglyceride and 85-90 mg/mL of D-α-tocopheryl polyethylene glycol succinate.

In a further embodiment, the oral formulation is a delayed-release soft gelatin capsule.

In another embodiment, the oral formulation is an extended-release soft gelatin capsule.

Additional aspects and/or embodiments of the invention will be provided, without limitation, in the detailed description of the invention that is set forth below.

DETAILED DESCRIPTION OF THE INVENTION

Set forth below is a description of what are currently believed to be preferred aspects and/or embodiments of the claimed invention. Any alternates or modifications in function, purpose, or structure are intended to be covered by the appended claims. As used in this specification and the appended claims, the singular forms "a," "an," and "the" include plural referents unless the context clearly dictates otherwise. The terms "comprise," "comprised," "comprises," and/or "comprising," as used in the specification and appended claims, specify the presence of the expressly recited components, elements, features, and/or steps, but do not preclude the presence or addition of one or more other components, elements, features, and/or steps.

As used herein, the term "patient" is meant to refer to any organism that is infected with or at risk of infection with a coronavirus. Such patient may include human patients and/or animal patients.

Nordihydroguaiaretic acid (NDGA) is the main metabolite of the creosote bush, *Larrea tridentata*, a chaparral or greasewood in the United States and as gobernadora or hediondilla in Mexico. NDGA is a natural polyphenol-bearing O-dihydroxy (catechol) with four phenolic hydroxyl groups with a molecular weight of 302.37 and a chemical structure according to Formula (1):

(1)

L. tridentata also contains 3'-O-methyl NDGA, a natural NDGA derivative with one methoxyl side chain and three hydroxyl side chains (rather than the four hydroxyl groups found on NDGA). Tetra-O-methyl NDGA, also known as terameprocol (TMP), is a synthetic tetra-methylated derivative NDGA and a transcription inhibitor with a molecular weight of 470.51 and a chemical structure according to Formula (2):

(2)

TMP competes with the transcription factor Sp1 for specific Sp1 DNA binding domains within gene promoter regions during DNA synthesis. While not intending to be bound by theory, it is believed that in virally-infected cells, TMP blocks the Sp1 binding site and suppresses Sp1-regulated viral promoter activity and gene expression, thereby inhibiting viral transcription and replication of virally infected cells.

Other synthetic and semi-synthetic NDGA derivatives include tetra acetyl NDGA, which has four acetyl groups ($COCH_3$) at positions 3, 4, 3', and 4'; maltose-tri-O-methyl NDGA, a water-soluble derivative of NDGA; tetra-O-glycyl NDGA, another water-soluble derivative of NDGA; bis-cyclic sulfate NDGA; bis-cyclic carbonate NDGA; methylenedioxyphenyl NDGA; and tetra acetate NDGA. Further NDGA derivatives may be prepared by adding an R group to one or more of positions 2, 3, 4, 5, 6, 2', 3', 4', 5', and 6' in the NDGA structure of Formula (1). Examples of R groups that may be added to one or more positions of Formula (1) to form NDGA derivatives include, without limitation, methyl, ethyl, acetyl, butyryl, isobutyryl, valeryl, hexanoyl, propionyl, piperidin-1-yl, acetonide, fluoro, morpholino, hydroxyl, methoxyl, hydroxy-methoxyl, dimethyl, dihydroxyl, dimethoxyl, dimethylamino, diethylamino, trimethoxyl, groups, chlorine, bromine, nitrite, amino, and acetamido. Additional NDGA derivatives may have an R group with one or more of the following: $(CH_2)_x Hal$ where x is an integer of 1-10 and Hal is a halogen atom (e.g., Cl, F, Br, I); $(CH_2CH_2O)$ where y is an integer of 1-10; and a carbamate-group. It should be understood that other NDGA derivatives may be made by adding different R groups to the NDGA of Formula (1). Techniques to produce such derivatives will be known to those of skill in the art.

The present invention is directed to NDGA derivatives that inhibit in vitro replication of coronaviruses. Examples of coronaviruses that may be subject to treatment with NDGA derivatives, include, without limitation, human coronavirus NL63 (HCoV-NL63), human coronavirus 229E (HCoV-229E), human coronavirus OC43 (HCoV-OC43), human coronavirus HKU1 (HCoV-HKU1), Middle East respiratory syndrome-related coronavirus (MERS-CoV), severe acute respiratory syndrome coronavirus (SARS-CoV-1), and severe acute respiratory syndrome coronavirus 2 (SARS-CoV-2), the latter of which causes coronavirus disease 2019 (COVID-19). The following discussion will reference TMP as an exemplary NDGA derivative; however, it is to be understood that the effects of TMP may be obtained with other natural or synthetic NDGA derivatives, such as 3'-O-methyl NDGA, tetra-O-methyl NDGA, and any other NDGA derivatives that compete with the transcription factor Sp1 for Sp1 DNA binding domains with gene promoter regions during DNA synthesis.

Figure 1:
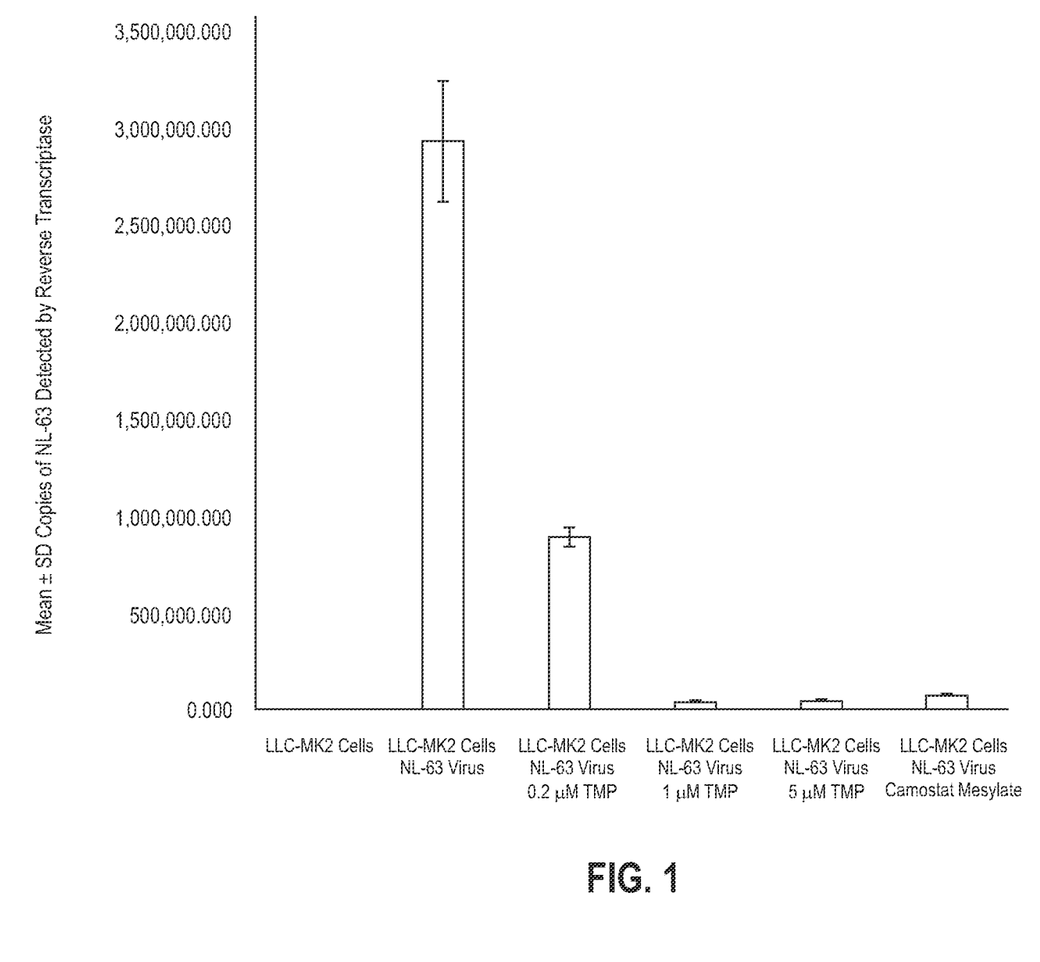
FIG. 1 is a bar graph showing the number of copies of HCoV-NL63 RNA measured 48 hours after HCoV-NL63 infection of cultured rhesus monkey kidney epithelial (LLC-MK2) cells without anti-viral treatment (negative control), with terameprocol (TMP) treatment at 0.2 µM, 1 µM, and 5 µM (anti-viral experimental), and with camostat mesylate (CM) treatment (positive control).

With reference to FIG. 1 (Example 1), LLC-MK2 cells (rhesus monkey kidney epithelial cells) were infected with NL63, treated with 0.2 μM, 1 μM, and 5 μM of TMP, and tested after 48 hours for the presence of NL63 viral RNA. NL63-infected LLC-MK2 cells without treatment were used as the negative control and NL63-infected LLC-MK2 cells treated with camostat mesylate (CM) were used as the positive control. As is known to those of skill in the art, CM is an antiviral agent that prevents infection by interfering with viral receptors within cells. Within the context of the present invention, the anti-viral activity of TMP differs from that of CM in that TMP interferes with the replication of SARS-CoV-2 within a cell. TMP is thus an agent that provides a different mode of action than CM for the treatment of patients infected with SARS-CoV-2. As shown in FIG. 1, treatment of NL3-infected LLC-MK2 cells with TMP showed a linear response that plateaued at 1 μM TMP. Treatment of the infected cells with 0.2 μM of TMP resulted in a partial reduction in viral activity after 48 hours while treatment with both 1 μM and 5 μM TMP showed almost no viral activity after 48 hours and no discernable cell toxicity resulting from the TMP treatment. As shown in FIG. 1, the NL63 infected negative control cells (no treatment) contained 2,931,946+390,851 (mean+standard deviation) copies of viral RNA while treatment of the NL63 infected cells with 0.2 μM TMP reduced the viral RNA copy number to 50,882+2,296 (mean+standard deviation; P=0.004 versus negative control by T-Test).

Figure 2:
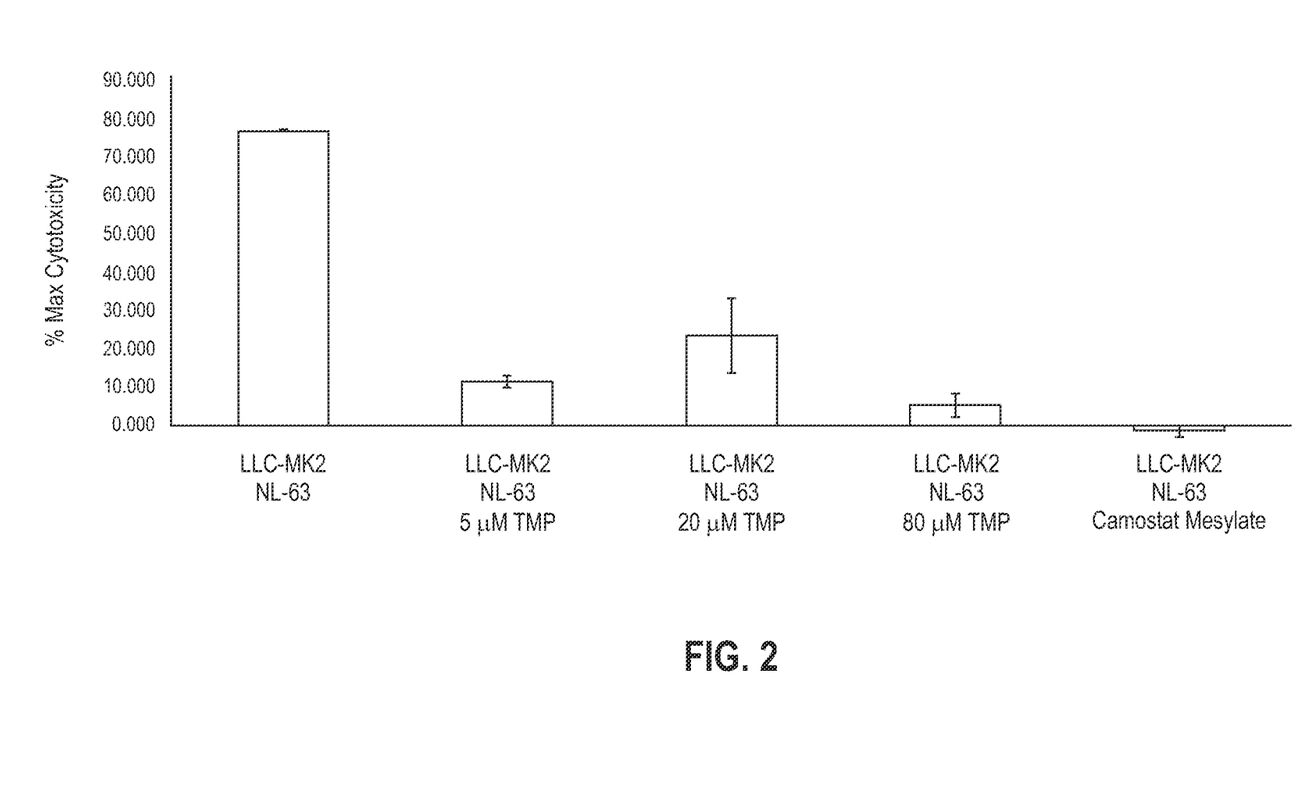
FIG. 2 is a bar graph showing the results of a cytotoxicity assay conducted five days after HCoV-NL63 infection of cultured LLC-MK2 cells without antiviral treatment (negative control), with TMP treatment at 5 µM, 20 µM, and 80 µM (anti-viral experimental), and with CM treatment (positive control). Cell cytotoxicity in response to the infection and/or the treatment was determined via lactate dehydrogenase (LDH) release in the cell supernatant.

With reference to FIG. 2 (Example 2), the exposure time of TMP on NL63-infected LLC-MK2 cells was measured to determine if long-term exposure to TMP could result in cell cytotoxicity. Cytotoxicity to the host cells can be caused by viral infection, which causes cell lysis, or by toxicity of test compounds to host cells. Cytotoxicity is measured by the release of lactate dehydrogenase (LDH), a cellular housekeeping enzyme, and its conversion of a colored substrate in the final reaction. Cells that die or lyse release LDH into the extracellular milieu; thus, the more LDH that is released by dying cells, the higher the LDH reading. As shown in FIG. 2, exposure of LLC-MK2 cells to NL63 without treatment (the negative control) showed that close to 80% of the cells in the sample lysed after five days, while NL63-infected LLC-MK2 cells treated with CM (the positive control) showed no cell toxicity after five days. When NL63-infected LLC-MK2 cells were treated with 5 μM TMP, the cell samples showed only 10% cell lysis after five days. A higher treatment dosage of 20 μM TMP resulted in 20-30% cell lysis after five days. Increasing the treatment does to 80 μM TMP resulted in the cells separating from the plate resulting in a lower LDH value than if the cells had remained on the plate.

Figure 3:
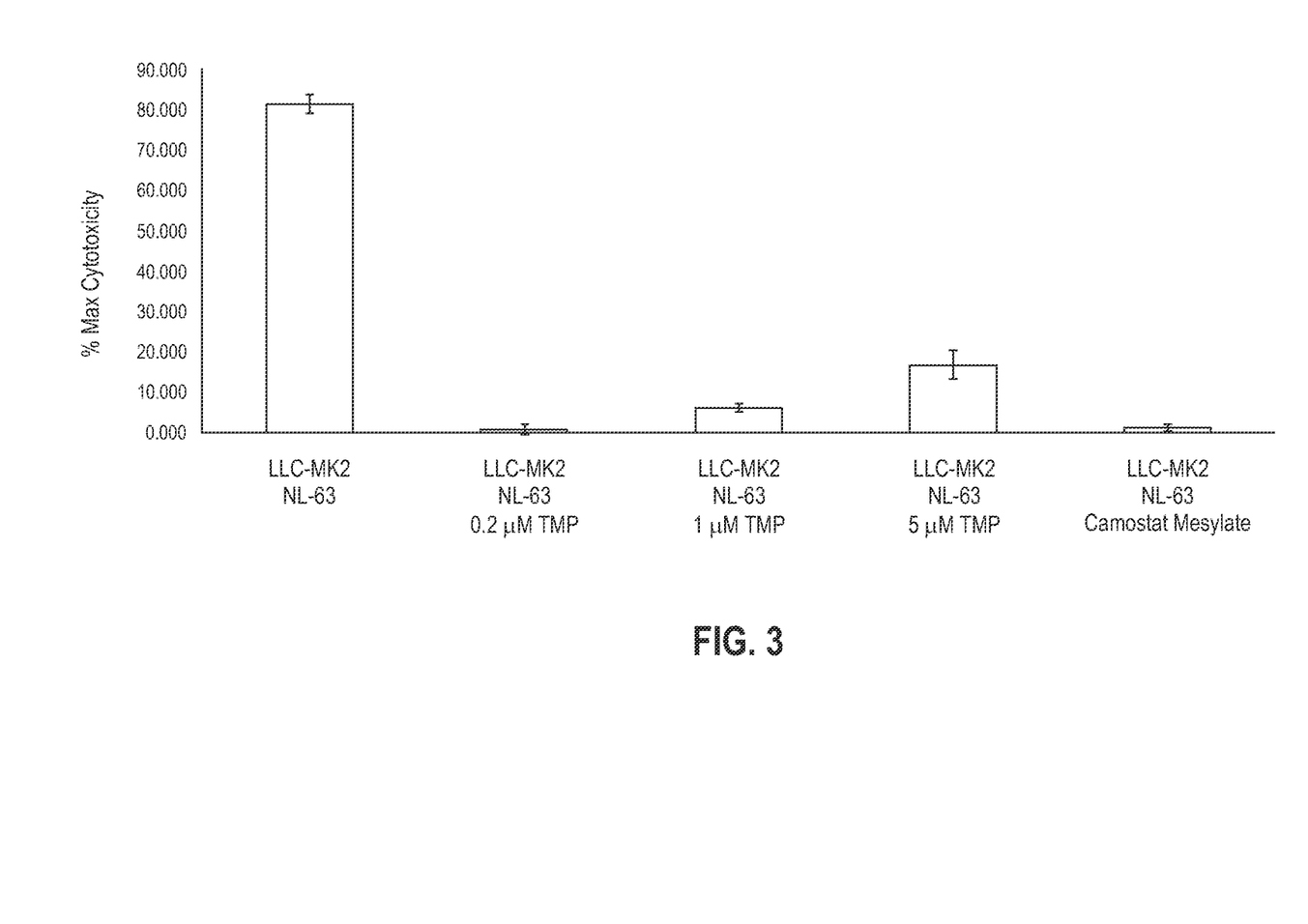
FIG. 3 is a bar graph showing the results of a cytotoxicity assay conducted five days after HCoV-NL63 infection of cultured LLC-MK2 cells without antiviral treatment (negative control), with TMP treatment at 0.2 µM, 1 µM, and 5 µM (anti-viral experimental), and with CM treatment (positive control). Cell cytotoxicity in response to the infection and/or the treatment was determined via lactate dehydrogenase (LDH) release in the cell supernatant.

With reference to FIG. 3 (Example 2), reducing the TMP concentration in the NL63-infected LLC-MK2 cells to 0.2 µM TMP showed that only 1-2% of the cells in the sample lysed, which is comparable to the results for the positive CM control. Increasing the concentration of TMP raised the cytotoxicity of the sample to approximately 8% cell lysis. Treatment with 5 µM TMP produced a cytotoxicity result of close to 20% cell lysis, which is twice as high as that shown for the 5 µM TMP treatment from FIG. 2. The results of FIGS. 2 and 3 show that the dosage of the TMP in vitro must be carefully calibrated to avoid treatment-related cell toxicity.

Figure 4A:
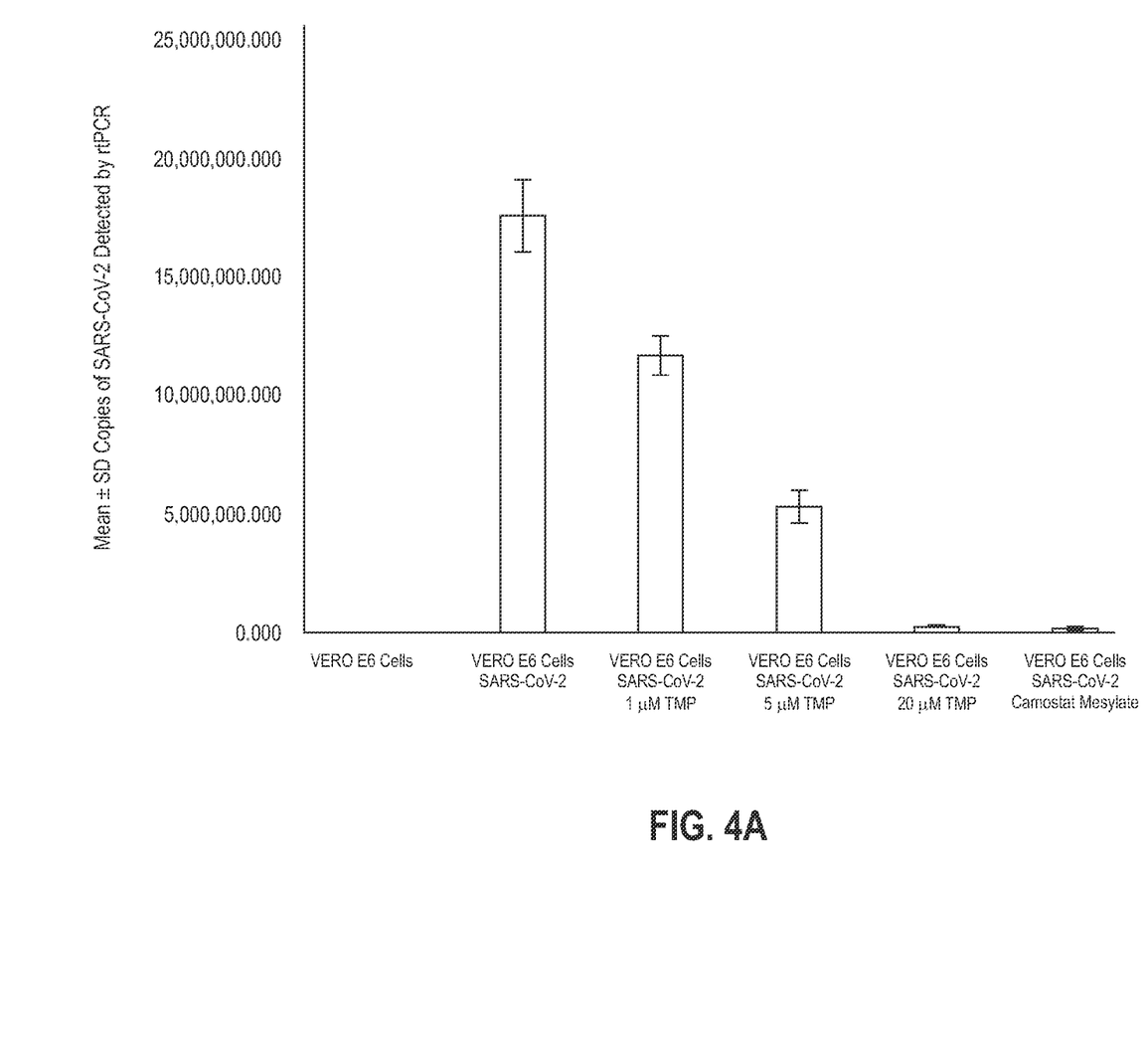
FIGS. 4A-C are bar graphs for three separate experiments showing the number of copies of SARS-CoV-2 coronavirus RNA measured 48 hours after SARS-CoV-2 infection of cultured African green monkey kidney epithelial (Vero E6) cells without anti-viral treatment (negative control), with TMP treatment at 1 µM, 5 µM, and 20 µM (anti-viral experimental), and with CM treatment (positive control).
Figure 4B:
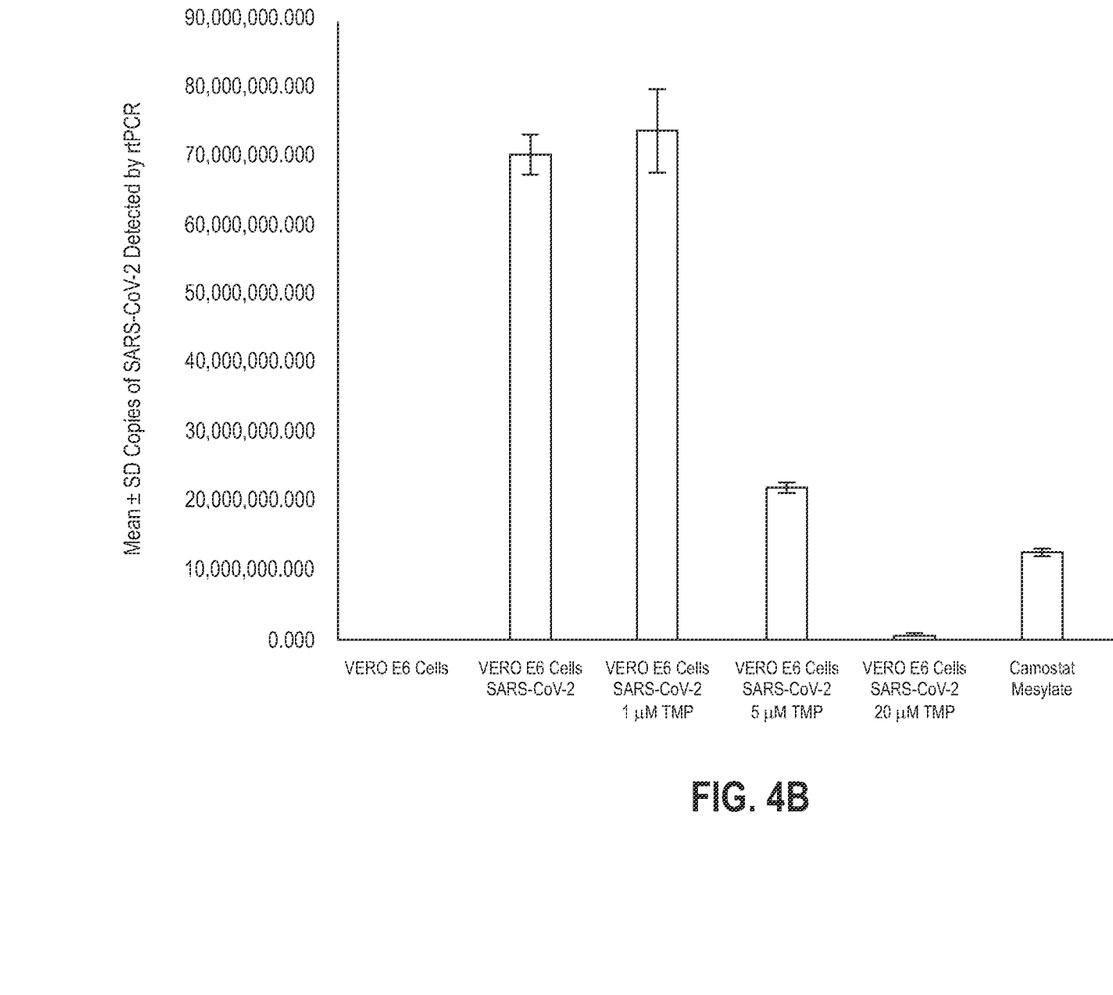
Figure 4C:
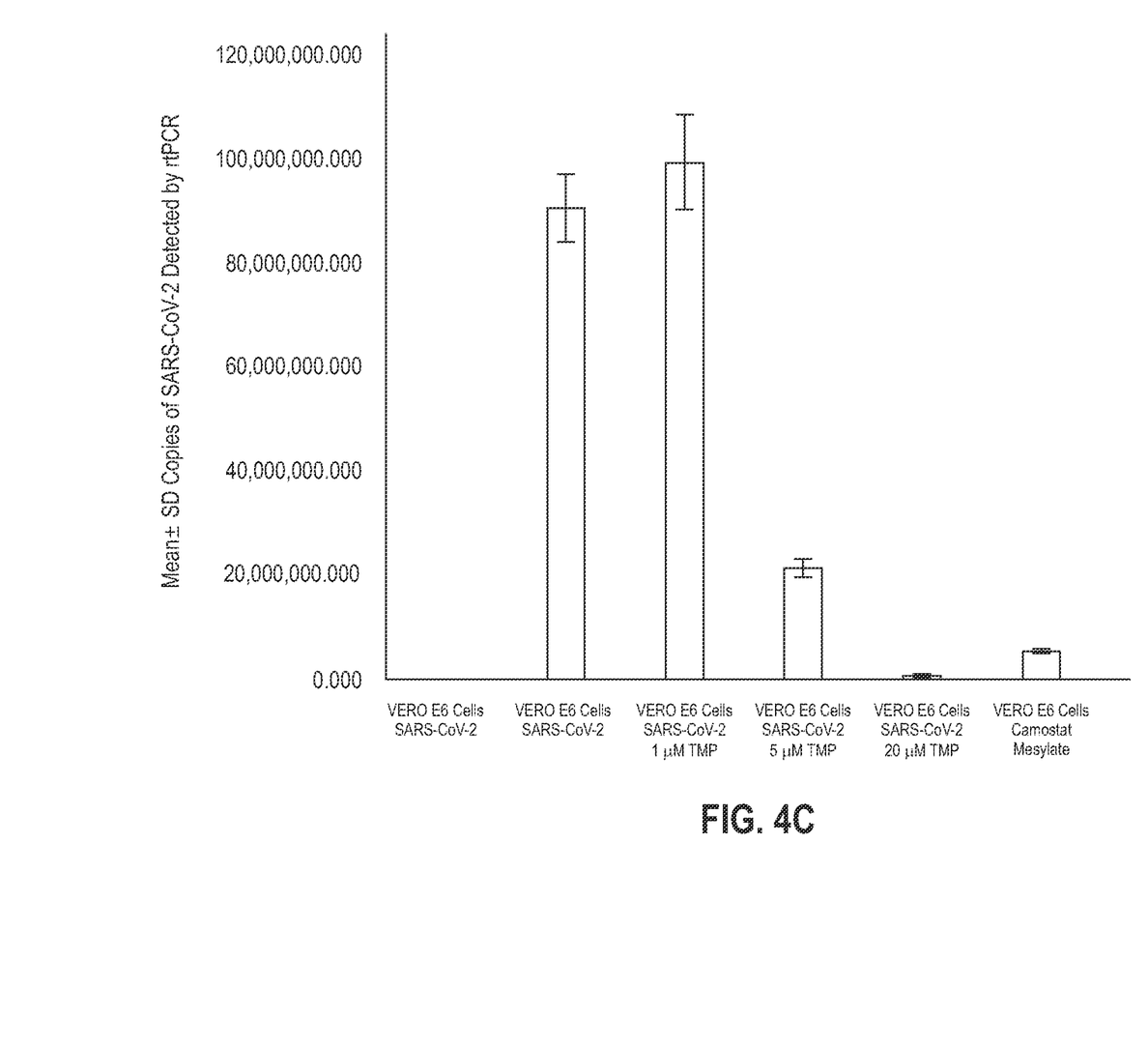

With reference to FIG. 4A (Example 3), Vero E6 cells (African green monkey kidney epithelial cells) were infected with SARS-CoV-2, treated with 0.2 µM, 1 µM, and 5 µM of TMP, and tested after 48 hours for the presence of SARS-CoV-2 RNA. Uninfected and untreated Vero E6 cells were used as a negative control and CM-treated infected cells were used as a positive control. Here, the TMP treatment showed a linear dose response where an increase in TMP treatment resulted in a decrease in viral replication. Notably, the 20 µM TMP treatment showed almost zero viral replication after 48 hours, comparable to the measured viral replication for the CM positive control. FIGS. 4B and 4C show two additional runs of the same TMP treatment regime shown in FIG. 4A, but instead of a linear response, FIGS. 4B and 4C show a non-linear response where treatment of SARS-CoV-2-infected Vero 6 cells with 1 µM TMP showed an increase in viral activity, while treatment with 5 µM TMP showed zero viral replication. Treatment with 20 µM TMP showed a reduction in viral replication comparable to the CM-treated positive control and no discernable cell toxicity resulting from the TMP treatment. While FIGS. 4A-4C show variability with respect to TMP-treated SARS-CoV-2-infected cells, the results show 5 µM as an optimal TMP treatment range for SARS-CoV-2-infected Vero E6 in vitro.

Figure 5:
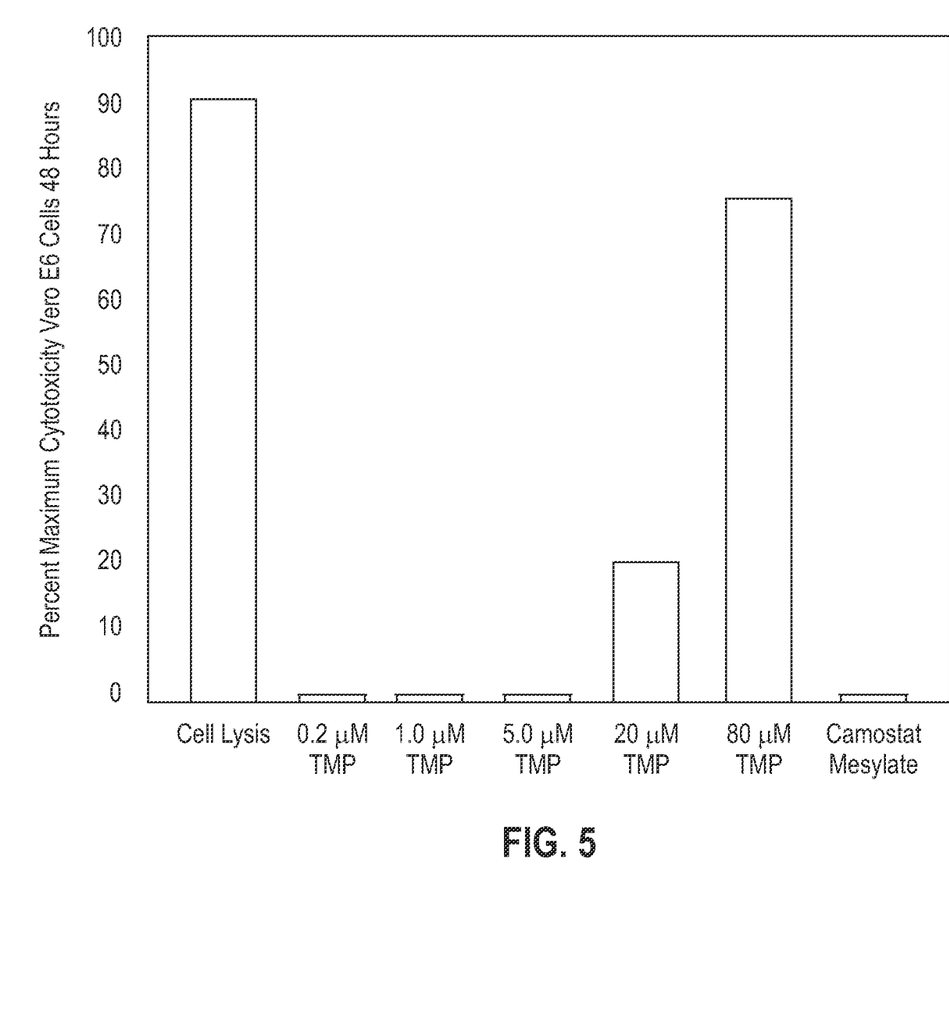
FIG. 5 is a bar graph showing the percent maximum toxicity of Vero E6 cells as measured by cell lysis for SARS-CoV-2 infected cells without treatment (negative control), with TMP treatment of 0.2 µM, 1.0 µM, 5 µM, 20 M, and 80 µM, and with CM treatment (positive control).

With reference to FIG. 5 (Example 3), Vero E6 were infected with SARS-CoV-2 virus, treated with 0.2 µM, 1.0 µM, 5.0 µM, 20 µM, and 80 µM of TMP, and tested for cell cytotoxicity using monoclonal antibodies after 48 hours. Infected Vero E6 cells without treatment were used as a negative control and infected Vero E6 cells treated with CM were used as a positive control. Here, the cells were tested for cytotoxicity via the formation of plaques identified with a monoclonal antibody. As expected, the negative control produced the highest number of plaques (89%) with the 80 μM TMP treatment also showing a high percentage of cell lysis. Cell cytotoxicity at 20 μM TMP was reduced in comparison to the 80 μM treatment while the TMP treatment at 0.2 μM, 1.0 μM, and 5 μM was comparable to the positive control in showing no appreciable cytotoxic effects.

With reference to FIG. 6 (Example 4), the TMP-treatment protocol for the Vero E6 cells was repeated with Calu-3 cells (human non-small-cell lung cancer cells) infected with SARS-CoV-2. Infected Calu-3 cells without treatment were used as a negative control and infected Calu-3 cells treated with CM were used as a positive control. A monoclonal antibody was used to identify cell cytotoxicity. With this cell line, 5 μM TMP showed a 25% reduction in the mean number of copies of SARS-CoV-2 when compared to the negative control, while the 20 μM and 40 μM TMP-treatments, as well as the CM negative control, show almost zero viral replication. With regard to cell cytotoxicity, the treatment of the infected Calu-3 cells with 5 μM and 20 μM TMP resulted in non-detectable cytotoxicity and only slightly increased cytotoxicity with 40 μM TMP.

The results of FIGS. 1-6 indicate that different coronavirus-infected cell lines all respond positively to TMP treatment, but that different cells lines may require different TMP dosages to show the most positive anti-viral effects while avoiding treatment cytotoxicity. Because it is believed that TMP binds to nuclear SP1 sites, it is likely that TMP inhibition of SARS-CoV-2 RNA is the result of TMP binding to SP1 regulated genes.

NDGA derivatives may be hydrophilic or hydrophobic. The solubility of hydrophobic NDGA derivatives may also be increased by decreasing the particle size of the NDGA derivatives from crystalline microparticles to solid colloidal nanoparticles with a size in the range of 1-100 nanometers. The formation of the nanoparticles from the larger crystalline particles may be achieved by top-down mechanical break-down of the larger particles through milling or by bottom-up assembly of the small nanoparticles through chemical vapor deposition. NDGA derivatives that have been reduced to nanoparticles have improved bioavailability and biodistribution control, enhanced absorption and efficiency, and reduced drug toxicity. Hydrophilic NDGA derivatives may also benefit from the improved bioavailability inherent in nanoparticle colloid dispersions.

To form IV or oral pharmaceuticals, the NDGA derivatives may be solubilized with compounds selected from the group consisting of (2-hydroxypropyl)-β-cyclodextrin (HPBCD), medium chain triglycerides (MCTs), glyceryl monooleate, D-at-tocopheryl polyethylene glycol succinate (TPGS), dimethylacetamide (DMA), dimethylsulfoxide (DMSO), polypropylene glycol (PPG), polyethylene glycol 400 (PEG with an average Mw of 400), polysorbate 20 (sold commercially sold as TWEEN® 20, Croda Americas LLC, Wilmington, Del., USA), naringin (a flavanone-7-O-glycoside), macrogol-15-hydroxystearate (sold commercially as KOLLIPHOR® HS 15 [previously Solutol HS 15], BASF SE, Ludwingshafen am Rhein, Germany), and combinations thereof. MCTs are triglycerides with two or three fatty acids having an aliphatic tail of medium chain fatty acids (MCFAs) with 6-12 carbon atoms. Examples of MCFAs include caproic acid (C6), caprylic acid (C8), capric acid (C10), and lauric acid (C12). One commercially sold MCT is MIGLYOL® 812N (Cremer Oleo GmbH, Hamburg, Germany). In order to maximize solubility and prevent precipitation of the NDGA derivative upon dilution, alcohols, surfactants and pH modifiers may be added to the solubilized NDGA derivative.

In one embodiment, an IV formulation comprises the NDGA derivative solubilized as an intact compound or as a solid nanoparticle colloid as described herein. The amount of NDGA derivative that will be intravenously administered to a patient will range from 0.1-50 μM. Where the NDGA derivative is TMP, the IV formulation may have 1-10 mg/mL TMP in an aqueous solution comprising 20-50% (2-hydroxypropyl)-1-cyclodextrin (HPBCD). An exemplary, but non-limiting, IV formulation may have 6 mg/mL TMP in an aqueous solution comprising 30% HPBCD.

In another embodiment, an oral formulation comprises the NDGA derivative as an intact compound or as a solid nanoparticle colloid as described herein. The amount of NDGA derivative that will be orally administered to a patient will range from 0.1-100 μM. Where the NDGA derivative is TMP, the oral formulation may have 100-500 mg/mL TMP in a suspension comprising a medium chain triglyceride (MCT) and D-α-tocopheryl polyethylene glycol succinate CTPGS). The amount of TPGS in the suspension may be in the range of 50-100 gm/mL. An exemplary, but non-limiting oral formulation may have 300 mg/mL of TMP in a suspension comprising an MCT and 85-90 mg/mL of TPGS.

The oral dosage forms for the NDGA derivatives described herein may be formulated as tables, capsules, or soft gel capsules (softgels) for immediate release (drug is release immediately after administration) or modified release (drug release occurs some period of time after administration or for a prolonged period of time or to a specific target in the body). Examples of modified release include, without limitation, delayed release (drug is released only at some point after the initial administration) and extended release (release of the drug is prolonged to reduce dosing frequency). Extended-release dosage forms include sustained release dosage forms (the drug is delivered at a certain concentration over a specified period of time) and controlled release dosage forms (the release of the drug is based on constant plasma concentrations of the drug and not on the timing of release). Where the dosage form is a modified release capsule, the polymers used to prepare the modified release characteristics of the dosage form are incorporated into the granules that are placed within the capsule shell, the latter of which is typically made from gelatin or hydroxymethylcellulose (HPMC). The release characteristics of modified release dosage forms may be achieved through reservoir systems, where suitable polymers are used to coat a tablet, softgel, or the granules of a capsule, or through matrix systems, where the drug is dissolved or dispersed with the polymer. For delayed release dosage forms, the oral formulations are generally enteric coated with pH sensitive polymers such that that the drug is released in the high pH environment of the small intestine, rather than the low pH environment of the stomach. For extended-release dosage forms, an oral formulation may be prepared by incorporating an active agent into matrix comprising a suitable polymer. Examples of polymers that have been used for extended-release dosage forms include, without limitation, ethyl cellulose, cellulose acetate, cellulose acetate propionate, polymethacrylate, hypromellose acetate succinate, and combinations thereof.

In one embodiment, the NDGA derivative is formulated into a delayed-release oral formulation by enteric coating the oral dosage form with a pH sensitive polymer. In another embodiment, the NDGA derivative is formulated into an extended-release formulation by incorporating ethyl cellulose, or other suitable polymers, into the oral formulation. In an exemplary, but non-limiting embodiment, the NDGA derivative is TMP formulated into a delayed-release or an extended release softgel.

The descriptions of the various aspects and/or embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the aspects and/or embodiments, the practical application or technical improvement over technologies found in the marketplace, or to enable others of ordinary skill in the art to understand the aspects and/or embodiments disclosed herein.

EXPERIMENTAL

The following Examples are set forth to provide those of ordinary skill in the art with a complete disclosure of how to make and use the aspects and embodiments of the invention as set forth herein. While efforts have been made to ensure accuracy with respect to variables such as amounts, temperature, etc., experimental error and deviations should be considered. Unless indicated otherwise, parts are parts by weight, temperature is degrees centigrade, and pressure is at or near atmospheric. All components were obtained commercially unless otherwise indicated.

In the Examples that follow, the ORIG3N® 2019 Novel Coronavirus (COVID-19) Test (hereinafter "Orig3N Test") (Orig3n, Inc., Boston, Mass., USA) was used to measure viral RNA. Instructions for the Orig3n RT-PCR test, including primers and probes used for the test, can be accessed at https://www.fda.gov/media/136873/download. As disclosed therein, the Orig3n Test is a real-time reverse transcription polymerase chain reaction (RT-PCR) test that uses two primer and probe sets to detect two regions in the SARS-CoV-2 nucleocapsid (N) gene (N1 and N2), one primer and probe set for the universal detection of SARS-like coronaviruses (N3), and one primer and probe set to detect human RNase P in a clinical sample.

RNA extraction from 400 μL samples was performed with the MAG-BIND® Viral DNA/RNA 96 (Omega Bio-Tek, Inc., Norcross, Ga., USA). RNA samples were amplified and extended using a QUANTSTUDIO® 7 Flex (QS7) (Life Technologies Corp., Carlsbad, CA, USA) instrument with QUANTSTUDIO® Real-Time PCR software version 1.3. During the amplification process, the probe anneals to a specific target sequence located between the forward and reverse primers. During the extension phase of the PCR cycle, the 5' nuclease activity of Taq polymerase degrades the bound probe, causing the reporter dye (FAM) to separate from the quencher dye (BHQ-1), generating a fluorescent signal. Fluorescence intensity is monitored at each PCR cycle.

Example 1

In Vitro Analysis of TMP Treated NL63-Infected LLC-MK2 Cells

LLC-MK2 monkey epithelial cells were cultured as host cells for the NL63 coronavirus in 96-well cell culture plates using ATCC's recommended media conditions. The NL-63 virus was diluted to ~500 plaque forming units/mL with growth medium (Medium 199+2.0% Fetal Bovine Serum (FBS)). Cells were infected with virus for 1 hr. at 37° C., washed once with balanced salts solution, and fresh medium containing 10% FBS added. The cells were observed for the formation of cytopathic effects (CPE) and plaques (clear regions in cell monolayer caused by cell death) for 5 days. Dead cells were discarded and live cells were used for testing with TMP.

Stock solutions of TMP were prepared by dissolving TMP in 100% DMSO at 50 mM with warming at 70° C. for 3 hours. TMP was added to the NL63-infected LLC-MK2 cells in the following concentrations: 0.2 μM, 1 μM, and 5 μM. Untreated infected LLC-MK2 cells and infected LLC-MK2 cells treated with camostat mesylate (CM) were used as negative and positive controls, respectively. 48 hours following treatment with TMP, 400 μL of supernatant was collected from each plate well and viral RNA (no cellular RNA was collected) and virus copy number were measured determined from the extracted DNA by the ORIG3N RT-PCR test. FIG. 1 shows the mean±SD (standard deviation)

of the number of copies of NL63 coronavirus RNA measured from the cell supernatant.

Example 2

Cytotoxicity Analysis of TMP Treated Treatment on NL63-Infected LLC-MK2 Cells LLC-MK2 cells were inoculated with NL63 as provided in Example 1. The cells were tested for cytotoxicity through the release of lactate dehydrogenase (LDH), the latter of which was measured and quantified with an LDH assay multiplate reader. The cytotoxicity assay was performed three times and values for each treatment group and controls were averaged across assays, as show in FIGS. 2 and 3.

Example 3

In Vitro Analysis of TMP Treated SARS-CoV-2-Infected Vero E6 Cells

Vero E6 African green monkey kidney epithelial cells were cultured as host cells for the SARS-CoV-2 coronavirus in 96-well cell culture plates. 500-1500 units of SARS-CoV-2 virus in Eagle's minimal essential medium (EMEM) with 10% Fetal Bovine Serum (FBS), L-glutamine, and Na-pyruvate phosphate buffered saline was introduced to the Vero E6 cell culture wells as described in Ogando et al., Journal of General Virology (2020) (available at biorxiv.org/content/10.1101/2020.04.20.049924v1). The cells were observed for the formation of cytopathic effects and plaques (i.e., clear regions in cell monolayer caused by cell death) for 48 hours. Plaques were identified using a plaque assay with the mouse monoclonal antibody J2 (Ogando et al., supra). Viral RNA was also isolated from the media supernatant and virus copy number was determined by RT-PCR for estimation of virus copy number following treatment.

Stock solutions of TMP were prepared by dissolving TMP in 100% DMSO at 50 mM with warming at 70° C. for 3 hours. TMP was added to the SARS-CoV-2-infected Vero E6 cells in the following concentrations: 0.2 µM, 1 µM, 5 µM, 20 µM, and 80 µM. Untreated infected Vero E6 cells and infected Vero E6 treated with CM were used as negative and positive controls, respectively. 48 hours following treatment with TMP, 400 µL of supernatant was collected from each plate well and viral RNA (no cellular RNA was collected) and virus copy number were measured from the extracted DNA by the ORIG3N RT-PCR test for the 1 µM, 5 µM, and 20 µM TMP-treatment wells as well as for the negative and positive controls. Separately, cell lysis was measured for all five TMP-treatment wells as well as for the negative and positive controls. The assay was repeated two additional times. FIGS. 4A-4C show the mean±SD of the number of copies of SARS-CoV-2 RNA measured from the cell supernatant for the three assay runs of the Vero E6 cells. FIG. 5 shows the results of the cell lysis measurements.

Example 4

In Vitro Analysis of TMP Treated SARS-CoV-2-Infected Calu-3 Cells

Calu-3 human non-small-cell lung cancer cells were cultured as host cells for the SARS-CoV-2 coronavirus in 96-well cell culture plates. 500-1500 units of SARS-CoV-2 virus in Eagle's minimal essential medium (EMEM) with 10% Fetal Bovine Serum (FBS), L-glutamine, and Na-pyruvate phosphate buffered saline was introduced to the Vero E6 cell culture wells as described in Ogando et al., supra. The cells were observed for the formation of cytopathic effects and plaques (i.e., clear regions in cell monolayer caused by cell death) for 48 hours. Plaques were identified using a plaque assay with the mouse monoclonal antibody J2 (Ogando et al., supra). Viral RNA was also isolated from the media supernatant and virus copy number was determined by RT-PCR for estimation of virus copy number following treatment.

Figure 6:
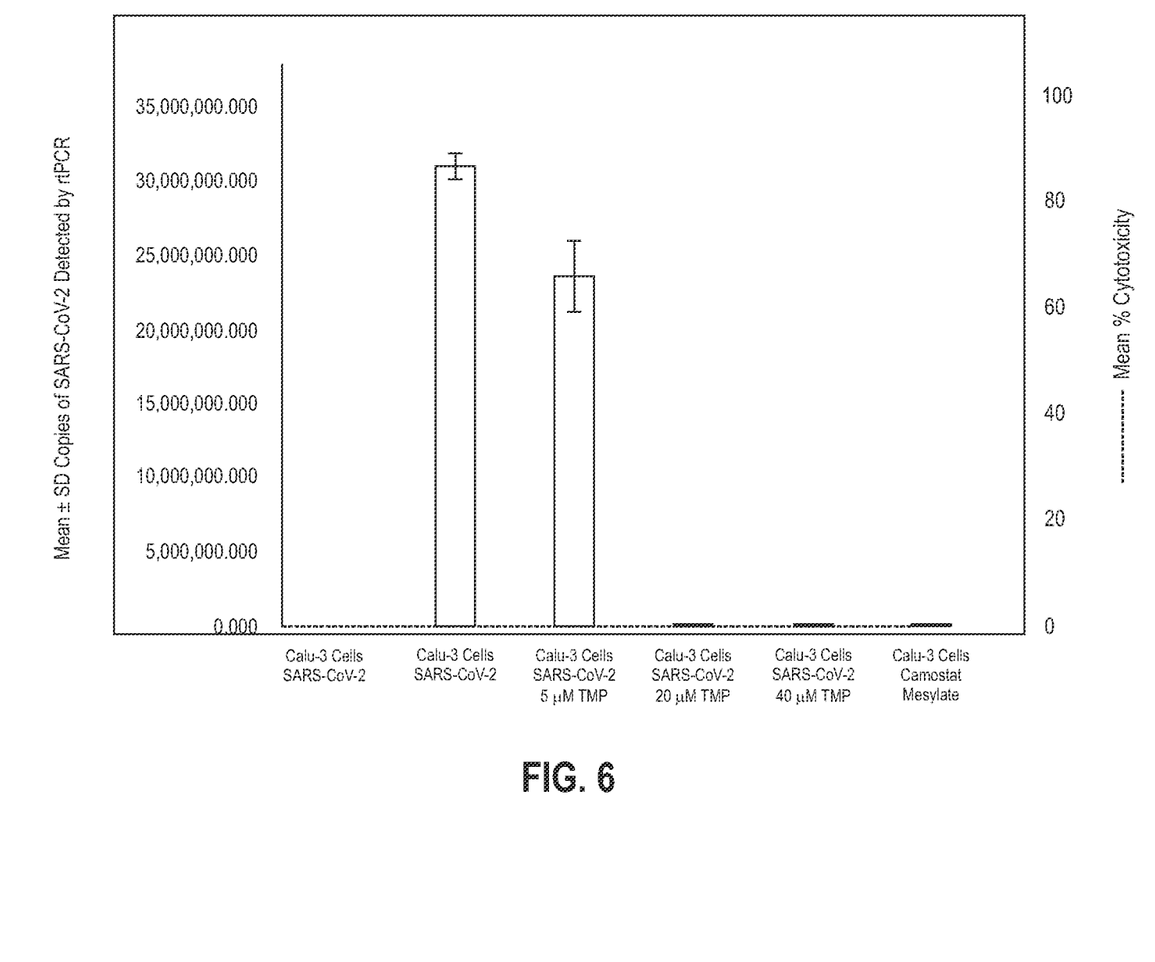
FIG. 6 is a bar graph showing the number of copies and associated cell cytotoxicity of SARS-CoV-2 coronavirus RNA measured 48 hours after SARS-CoV-2 infection of cultured human non-small-cell lung cancer (Calu-3) cells without anti-viral treatment (negative control), with TMP treatment at 5 µM, 20 µM, and 40 µM (anti-viral experimental), and with CM treatment (positive control).

Stock solutions of TMP were prepared by dissolving TMP in 100% DMSO at 50 mM with warming at 70° C. for 3 hours. TMP was added to the SARS-CoV-2-infected Vero E6 cells in the following concentrations: 5 µM, 20 µM, and 40 µM. Untreated infected Vero E6 cells and infected Vero E6 treated with CM were used as negative and positive controls, respectively. 48 hours following treatment with TMP, 400 µL of supernatant was collected from each plate well and viral RNA (no cellular RNA was collected) and virus copy number were measured determined from the extracted DNA by the ORIG3N RT-PCR test. The assay was repeated two additional times. FIG. 6 shows the mean±SD of the number of copies of SARS-CoV-2 RNA measured from the cell supernatant for the Calu-3 cells as well as the cytotoxicity results for the TMP treatment as measured by the number of plaques.

We claim:

1. A method comprising administering a nordihydroguaiaretic acid (NDGA) derivative to a patient infected with or at risk of infection with a coronavirus, wherein the NDGA derivative is selected from the group consisting of terameprocol, 3'-O-methyl NDGA, tetra acetyl NDGA, maltose-tri-O-methyl NDGA, tetra-O-glycyl NDGA, bis-cyclic sulfate NDGA; bis-cyclic carbonate NDGA; methylenedioxyphenyl NDGA; tetra acetate NDGA.

2. The method of claim 1, wherein the coronavirus is selected from the group consisting of human coronavirus NL63 (HCoV-NL63), human coronavirus 229E (HCoV-229E), human coronavirus OC43 (HCoV-OC43), human coronavirus HKU1 (HCoV-HKU1), Middle East respiratory syndrome-related coronavirus (MERS-CoV), severe acute respiratory syndrome coronavirus (SARS-CoV-1), and severe acute respiratory syndrome coronavirus 2 (SARS-CoV-2).

3. The method of claim 1, wherein administration of the NDGA derivative inhibits viral RNA replication.

4. The method of claim 1, wherein the NDGA derivative is formed into solid colloidal nanoparticles with a size in the range of 1-100 nanometers.

5. The method of claim 1, wherein the NDGA derivative is solubilized in a solution or suspension comprising a compound selected from the group consisting, (2-hydroxypropyl)β-cyclodextrin, medium chain triglycerides, glyceryl monooleate, D-α-tocopheryl polyethylene glycol succinate, dimethylacetamide, dimethylsulfoxide, polypropylene glycol, polyethylene glycol 400, polysorbate 20, naringin, macrogol-15-hydroxystearate, and combinations thereof.

6. The method of claim 1, wherein 0.1-50 µM of the NDGA derivative is formulated for intravenous administration.

7. The method of claim 1, wherein 0.1-100 µM of the NDGA derivative is formulated for oral administration.

8. A method comprising administering terameprocol (TMP) to a patient infected with or at risk of infection with a coronavirus.

9. The method of claim 8, wherein the coronavirus is selected from the group consisting of human coronavirus NL63 (HCoV-NL63), human coronavirus 229E (HCoV-229E), human coronavirus OC43 (HCoV-OC43), human coronavirus HKU1 (HCoV-HKU1), Middle East respiratory syndrome-related coronavirus (MERS-CoV), severe acute respiratory syndrome coronavirus (SARS-CoV-1), and severe acute respiratory syndrome coronavirus 2 (SARS-CoV-2).

10. The method of claim 8, wherein administration of the TMP inhibits viral RNA replication.

11. The method of claim 8, wherein the TMP is formed into solid colloidal nanoparticles with a size in the range of 1-100 nanometers.

12. The method of claim 8, wherein the TMP is solubilized in a solution or suspension comprising a compound selected from the group consisting (2-hydroxypropyl)β-cyclodextrin, medium chain triglycerides, glyceryl monooleate, D-α-tocopheryl polyethylene glycol succinate, dimethylacetamide, dimethylsulfoxide, polypropylene glycol, polyethylene glycol 400, polysorbate 20, naringin, macrogol-15-hydroxystearate, and combinations thereof.

13. The method of claim 11, wherein 0.1-50 μM of the TMP is formulated as a solution for intravenous administration.

14. The method of claim 13, wherein the TMP is solubilized in an aqueous solution comprising (2-hydroxypropyl)β-cyclodextrin.

15. The method of claim 13, wherein 1-10 mg/mL of TMP is solubilized in an aqueous solution comprising 20-50% (2-hydroxypropyl)β-cyclodextrin.

16. The method of claim 13, wherein 6 mg/mL of the TMP is solubilized in an aqueous solution comprising 30% (2-hydroxypropyl)β-cyclodextrin.

17. The method of claim 11, wherein 0.1-100 μM of the TMP is formulated for oral administration.

18. The method of claim 17, wherein the TMP is solubilized in a suspension comprising a medium chain triglyceride and D-α-tocopheryl polyethylene glycol succinate.

19. The method of claim 17, wherein 100-500 mg/mL of TMP is solubilized in a suspension comprising a medium chain triglyceride and 50-100 mg/mL of D-α-tocopheryl polyethylene glycol succinate.

20. The method of claim 17, wherein 300 mg/mL of TMP is solubilized in a suspension comprising a medium chain triglyceride and 85-90 mg/mL of D-α-tocopheryl polyethylene glycol succinate.

21. The method of claim 20, wherein the oral formulation is a delayed-release soft gelatin capsule.

22. The method of claim 20, wherein the oral formulation is an extended-release soft gelatin capsule.

* * * * *